(12) United States Patent
Suzuki et al.

(10) Patent No.: US 9,301,800 B2
(45) Date of Patent: Apr. 5, 2016

(54) ENDOSCOPIC TREATMENT TOOL

(75) Inventors: Tetsu Suzuki, Tokyo (JP); Naohisa Yahagi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 976 days.

(21) Appl. No.: 13/025,562

(22) Filed: Feb. 11, 2011

(65) Prior Publication Data

US 2011/0137123 A1 Jun. 9, 2011

Related U.S. Application Data

(63) Continuation of application No. PCT/JP2009/003769, filed on Aug. 6, 2009.

(30) Foreign Application Priority Data

Aug. 13, 2008 (JP) ................................. 2008-208715

(51) Int. Cl.
*A61B 18/14* (2006.01)
*A61B 1/005* (2006.01)
(Continued)

(52) U.S. Cl.
CPC ............. *A61B 18/1477* (2013.01); *A61B 1/005* (2013.01); *A61B 18/1492* (2013.01); *A61B 2017/0088* (2013.01); *A61B 2017/00269* (2013.01);
(Continued)

(58) Field of Classification Search
CPC ........... A61B 18/1492; A61B 18/1477; A61B 2018/00601; A61B 2018/00577; A61B 2018/1417; A61B 2018/1475; A61B 2018/00482; A61B 2017/00269; A61B 2017/0088; A61B 1/005

USPC ................................................ 606/41, 45–50
See application file for complete search history.

(56) References Cited

U.S. PATENT DOCUMENTS 4,708,137 A 11/1987 Tsukagoshi
5,085,659 A * 2/1992 Rydell ........................... 606/47
(Continued)

FOREIGN PATENT DOCUMENTS

EP 2 050 409 A1 4/2009
EP 2 168 516 A1 3/2010
(Continued)

OTHER PUBLICATIONS

European Search Report dated Apr. 5, 2013 from corresponding European Patent Application No. 09 80 6567.5.
(Continued)

*Primary Examiner* — Michael Peffley
(74) *Attorney, Agent, or Firm* — Scully, Scott, Murphy & Presser, P.C.

(57) ABSTRACT

The present invention relates to a flex-knife that enables a technique such as tissue excision to be carried out more easily, and is provided with: a rod-shaped high frequency knife which is endoscopically inserted into a body cavity and is for performing cutting procedures; a wire, the high frequency knife connected to the front end thereof; a sheath consisting of an insulating material, into which the wire is inserted; a main body, the back end of the sheath being connected thereto; and a slider to which the back end of the wire is fixed and which is disposed to the main body to enable sliding in the axial direction; wherein the high frequency knife has a large diameter part at its distal end, the large diameter part having an outer diameter that is larger than the inner diameter of the sheath.

8 Claims, 10 Drawing Sheets

(51) Int. Cl.
  *A61B 17/00* (2006.01)
  *A61B 18/00* (2006.01)
(52) U.S. Cl.
  CPC .................. *A61B2018/00107* (2013.01); *A61B 2018/00482* (2013.01); *A61B 2018/00601* (2013.01); *A61B 2018/1417* (2013.01); *A61B 2018/1475* (2013.01)

(56) References Cited

U.S. PATENT DOCUMENTS

| | | | | |
|---|---|---|---|---|
| 6,063,080 | A * | 5/2000 | Nelson et al. ................... | 606/41 |
| 6,190,384 | B1 * | 2/2001 | Ouchi ............................. | 606/47 |
| 6,733,496 | B2 * | 5/2004 | Sharkey et al. ................ | 606/41 |
| 2004/0167514 | A1 * | 8/2004 | Okada ............................. | 606/45 |
| 2004/0210215 | A1 * | 10/2004 | Okada ............................. | 606/45 |
| 2005/0072280 | A1 * | 4/2005 | Ono et al. ....................... | 83/13 |
| 2005/0215853 | A1 | 9/2005 | Ouchi | |
| 2006/0079873 | A1 * | 4/2006 | Scopton et al. ................. | 606/37 |
| 2007/0049921 | A1 | 3/2007 | Konishi et al. | |

FOREIGN PATENT DOCUMENTS

| | | |
|---|---|---|
| JP | S61-191012 | 11/1986 |
| JP | 08-299355 | 11/1996 |
| JP | 2004-313537 | 11/2004 |
| JP | 2005-329095 | 12/2005 |
| JP | 2006-280662 | 10/2006 |
| JP | 2006-326157 | 12/2006 |
| JP | 2007-44281 A | 2/2007 |
| JP | 2008-000386 | 1/2008 |
| JP | 2008-119253 A | 5/2008 |
| JP | 2008-119523 A | 5/2008 |
| WO | 2008/026689 A1 | 3/2008 |
| WO | 2009/062057 A2 | 5/2009 |

OTHER PUBLICATIONS

Notice of Reasons for Rejection dated Feb. 12, 2013 from corresponding Japanese Patent Application 2008-208715, together with an English language translation.
International Search Report dated Sep. 15, 2009.

* cited by examiner

ENDOSCOPIC TREATMENT TOOL

CROSS-REFERENCE TO RELATED PATENT APPLICATIONS

This application is a Continuation of International Application No. PCT/JP2009/003769, filed on Aug. 6, 2009, claiming priority based on Japanese Patent Application No. 2008-208715, filed on Aug. 13, 2008, the content of which is incorporated herein by reference in their entirety.

BACKGROUND

1. Technical Field

The present invention relates to an endoscopic treatment tool that is employed by insertion into the instrument channel of an endoscopic device.

2. Description of the Related Art

An endoscopic treatment tool is conventionally known which is inserted into a body cavity endoscopically, and is equipped with a needle knife (for example Japanese Unexamined Utility Model Application, First Publication No. S61-191012) or the like for excising mucosa, etc. through the transmission of a high-frequency current. In this type of endoscopic treatment tool, a cutting section, such as a needle knife or the like, for carrying out the procedure, is attached to the distal end of a wire that has been inserted into an insulated sheath which is inserted into the endoscope channel.

The cutting section is designed to be freely projected out from or retracted into the distal end of the sheath by manipulating an operating member to which the proximal end of the wire is fixed. The shape of the cutting section is typically a round rod-like form, or, as necessary, may be subjected to working to taper the distal end.

SUMMARY OF THE DISCLOSURE

The present invention has as its objective the provision of an endoscopic treatment tool that can facilitate execution of such techniques as tissue excision, etc.

The endoscopic treatment tool according to the present invention is provided with a rod-shaped cutting section which is endoscopically inserted into a body cavity and is for performing cutting procedures; a wire, at the distal end of which the cutting section is connected; a sheath which consists of an insulating material and into which the wire is inserted; a main body to which the back end of the sheath is connected; and a slider to which the back end of the wire is fixed and which is disposed to the main body to enable sliding in the axial direction; wherein the cutting section has a large diameter part at the distal end of the cutting section, the large diameter part having an outer diameter that is larger than the inner diameter of the sheath.

The large diameter part may have a semispherical part which is formed to be semispherical in shape and is provided on the distal end side, with the semispherical surface directed toward the distal end side; and a circular cylinder part which is provided to the proximal end side of the semispherical part so the axis thereof is parallel to the axis of the cutting section.

The endoscopic treatment tool according to the present invention may be further provided with a tubular distal member which has a through hole along the axis, and is attached to the distal end of the sheath. The inner diameter of the through hole may be designed to be smaller than the outer diameter of the large diameter part.

DETAILED DESCRIPTION

The endoscopic treatment tool (referred to simply as "treatment tool" hereinafter) according to a first embodiment of the present invention will be explained with reference to FIGS. 1 through 16B.

Figure 1:
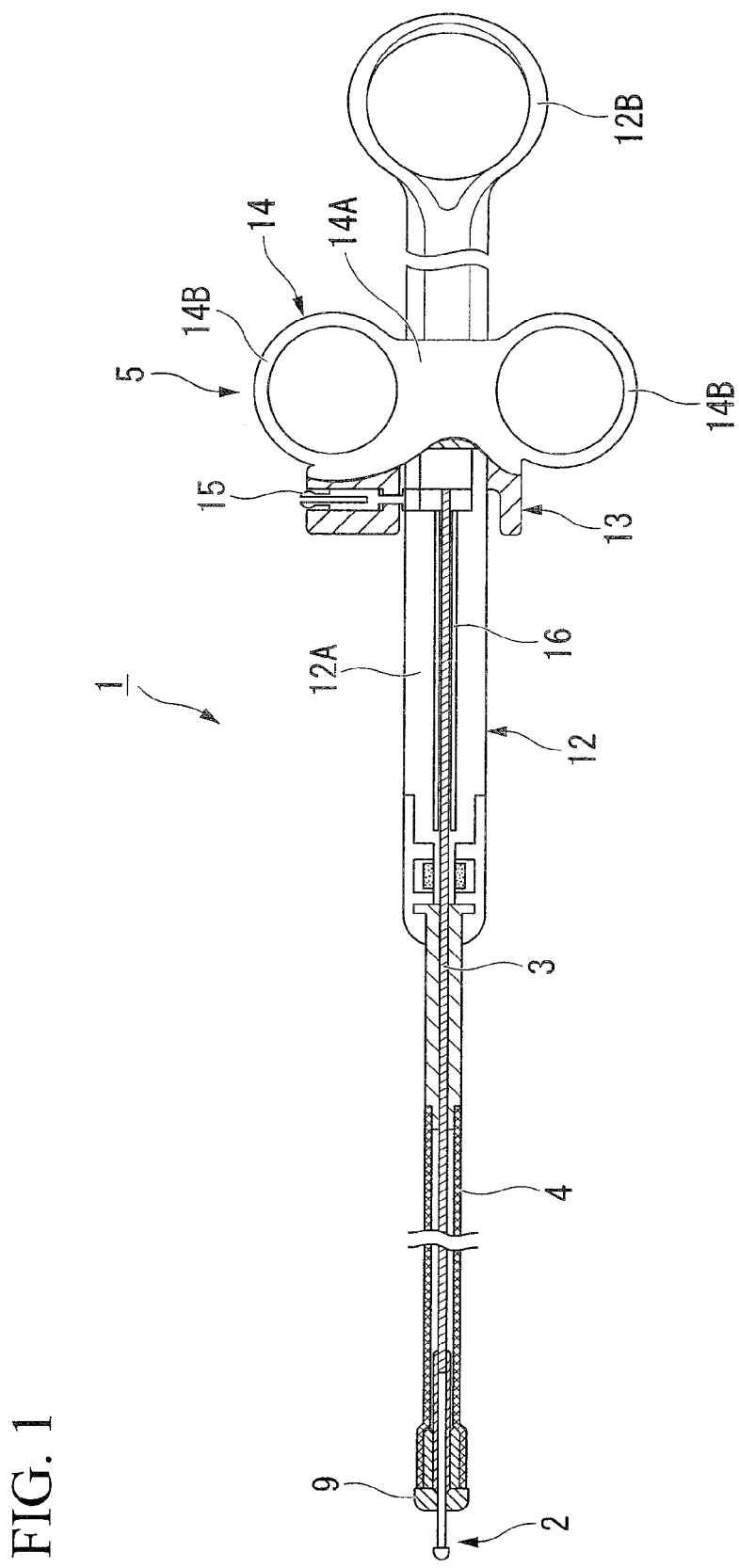
FIG. 1 is a view showing a treatment tool according to an embodiment of the present invention.

FIG. 1 is a cross-sectional view showing portions of the treatment tool 1 according to the first embodiment. The treatment tool 1 is provided with a wire 3, the front end of which is attached to a high frequency knife (cutting section) 2; a sheath 4 into which the knife 2 and the wire 3 are inserted; and an operator 5 for manipulating the wire 3 and the sheath 4.

The high frequency knife (referred to simply as "knife" hereinafter) is an approximately round rod-like member consisting of a conductor made of metal or the like. As will be explained hereinafter, this high frequency knife 2 is employed to carry out a cutting procedure to a tissue inside a body cavity through the transmission of high frequency current. The maximum length of projection of the knife 2 from the distal end of the sheath 4 may be appropriately set based on the type, etc. of tissue which is the target of the treatment tool 1. For example, in the case where using the treatment tool 1 on the stomach wall or similar tissue, it is desirable to set the maximum length of projection to around 2 millimeters (mm), which is less than the average thickness of the stomach wall.

Figure 2:
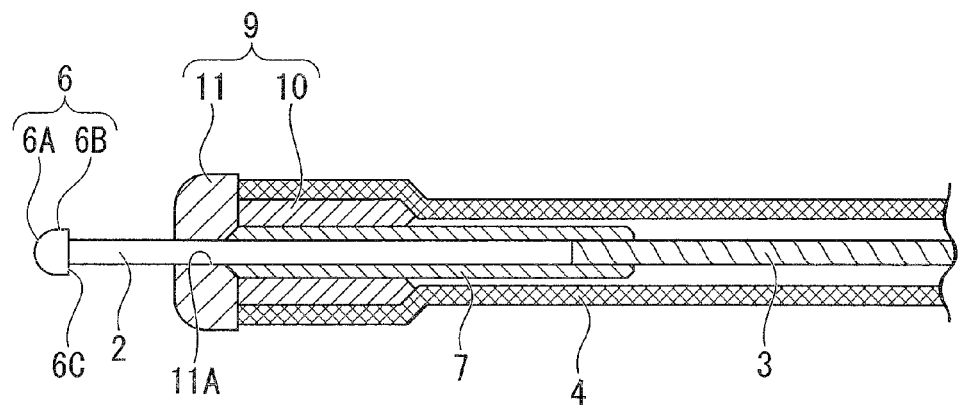
FIG. 2 is an enlarged cross-sectional view about the distal end of the same treatment tool.

FIG. 2 is an enlarged cross-sectional view about the distal end of the treatment tool 1. As shown in FIG. 2, the knife 2 has a large diameter part 6 at its the distal end which has an expanded diameter. The large diameter part 6 has a semispherical part 6A on its distal end side and a circular cylinder part 6B on the proximal end side of the semispherical part 6A. In other words, the outer surface of the distal end side of the large diameter part 6 forms a semispherical surface, while an outer peripheral surface which is substantially parallel to the axis of the knife 2 is formed to the proximal end side of the large diameter part 6.

In order to suitably increase the density of the high frequency current, the diameter of the knife 2, excluding the large diameter part 6, is formed to be thin, at around 0.3~0.5 mm, for example.

There are numerous points to consider in the design process with regard to a suitable diameter for the large diameter part 6. This will be discussed further below, however, for this reason, the diameter of the circular cylinder part 6B in the treatment tool 1 according to this embodiment is set to 0.6 mm, for example. In other words, the outer peripheral surface of the circular cylinder part 6B projects out in the radially outward direction around 0.1~0.15 mm more than the outer peripheral surface of the parts of knife 2 that have the usual diameter (i.e., the area closer to the proximal end side than the large diameter part 6). The proximal end 6C of the large diameter part 6 projects out to form an edge.

The wire 3 consists of a metal such as stainless steel, etc., which has superior torque transmissivity, The wire 3 is inserted into the sheath 4 via a connecting member 7, in an arrangement in which it is fixed in a unitary manner to the knife 2. The proximal end of the wire 3 extends to the operator 5.

The sheath 4 is a tubular member, consisting of a resin or the like, which is pliable and has insulating properties. By increasing thickness of the sheath 4, etc., the rigidity of the sheath 4 is slightly higher than that of as compared to the sheaths employed in the typical treatment tool, so that sheath 4 maintains a substantially perpendicular state in response to forces up to a specific extent, even when projected out some length from the distal end of the endoscope.

Figure 3:
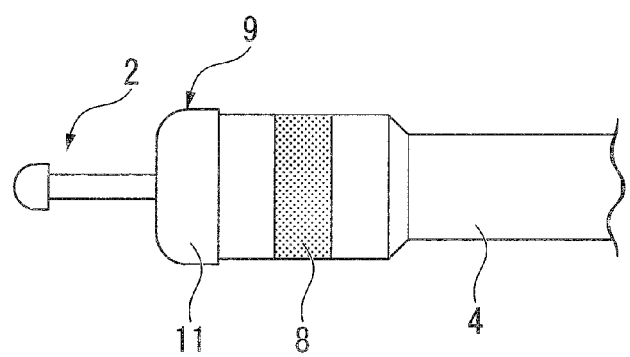
FIG. 3 is an enlarged view about the distal end of the same treatment tool.

As shown in FIG. 3, a marker 8 is provided about the circumference of the outer peripheral surface of the sheath 4. This marker 8 is for recognizing the extent to which the treatment tool 1 has advanced into the tissue at a position which is a specific distance from the distal end. The marker 8 may be provided to just a portion of or intermittently about the circumferential direction.

A substantially tubular distal member 9 is fixed in place to the front end of the sheath 4 by means of press fitting, etc. This distal member 9 is preferably formed of a member having insulating properties, such as ceramic, resin, rubber or the like. However, it may also be formed of a member in which an insulating coating, etc. has been applied to the surface of a metal or the like.

As shown in FIG. 2, the distal member 9 has a substantially cylindrical axis 10 which is inserted into the sheath 4, and a tip 11 which is exposed outside the sheath 4. The outer diameter of the axis 10 is designed to be larger than the inner diameter of the sheath 4. The distal end side of the sheath 4 into which the axis 10 is inserted has an outer diameter which is larger than the other areas of sheath 4. The tip 11 is a part which often comes into contact with the tissue, etc., inside the body cavity during the procedure. As such, the outer surface is formed to be curving, and to have a form which does not have angles or edges.

Figure 4:
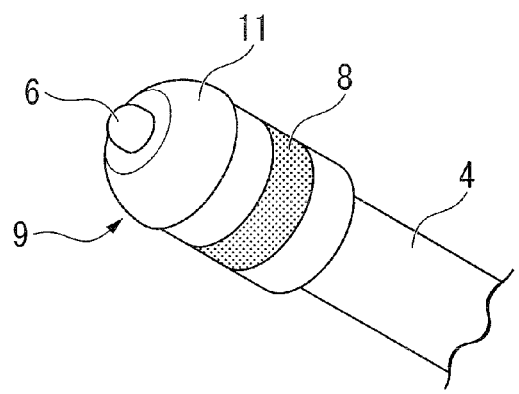
FIG. 4 is a view showing the distal end of the same treatment tool when the knife has been retracted.

A through hole 11A having a diameter which is substantially equal to the usual diameter of the knife 2 is formed approximately along the axial line. The knife 2 is inserted into the through hole 11A. The outer diameter of the large diameter part 6 is larger than the diameter of the through hole 11A. As a result, even if the knife 2 is fully retracted, it is not possible to house the large diameter part 6 within the sheath 4. Rather, as shown in FIG. 4, only the large diameter part 6 projects out from the tip 11.

The proximal end of the through hole 11A is formed of a slightly expanded diameter and can come into contact with the connecting member 7. For this reason, even if the knife 2 is advanced fully, the knife 2 cannot advance further once the connecting member 7 has come into contact with the distal member 9. Accordingly, the set maximum length of projection does not project out from the sheath.

Returning to FIG. 1, the operator 5 is provided with a main body 12 to which the sheath 4 is affixed, and a slider 13 to which the proximal end of the wire 3 is affixed.

The main body 12 is an approximately rod-shaped member. A guide groove 12A for sliding the slider 13 is provided extending in the axial direction. A ring 12B into which the operator places his finger is provided to the back end of the main body 12.

In the slider 13, a plug 15, which is connected to a high frequency power source not shown in the figures, is attached to an operating member 14 which has a cylindrical part 14A that surrounds the outer periphery of the main body 12 and a handle 14B on which the fingers of the operator rest during operation. The back end of the wire 3, which is extended inside the guide groove 12A, is inserted into a buckling preventing pipe 16 which is formed of a rigid material. The back ends of the wire 3 and the buckling preventing pipe 16 are connected and fixed in place to the plug 15 by a fixing means such as a screw, etc., not shown in the figures. In other words, the slider 13 and the wire 3 are attached to the main body 12 to permit sliding along the axial direction in the guide groove 12A.

The action when using a treatment tool 1 formed as described above will now be explained using as an example the case where excising stomach mucosa.

The inserted section of the endoscope is introduced into the body cavity of a patient and the distal end of the inserted section is moved near the tissue on which the procedure is to be performed.

Figure 5:
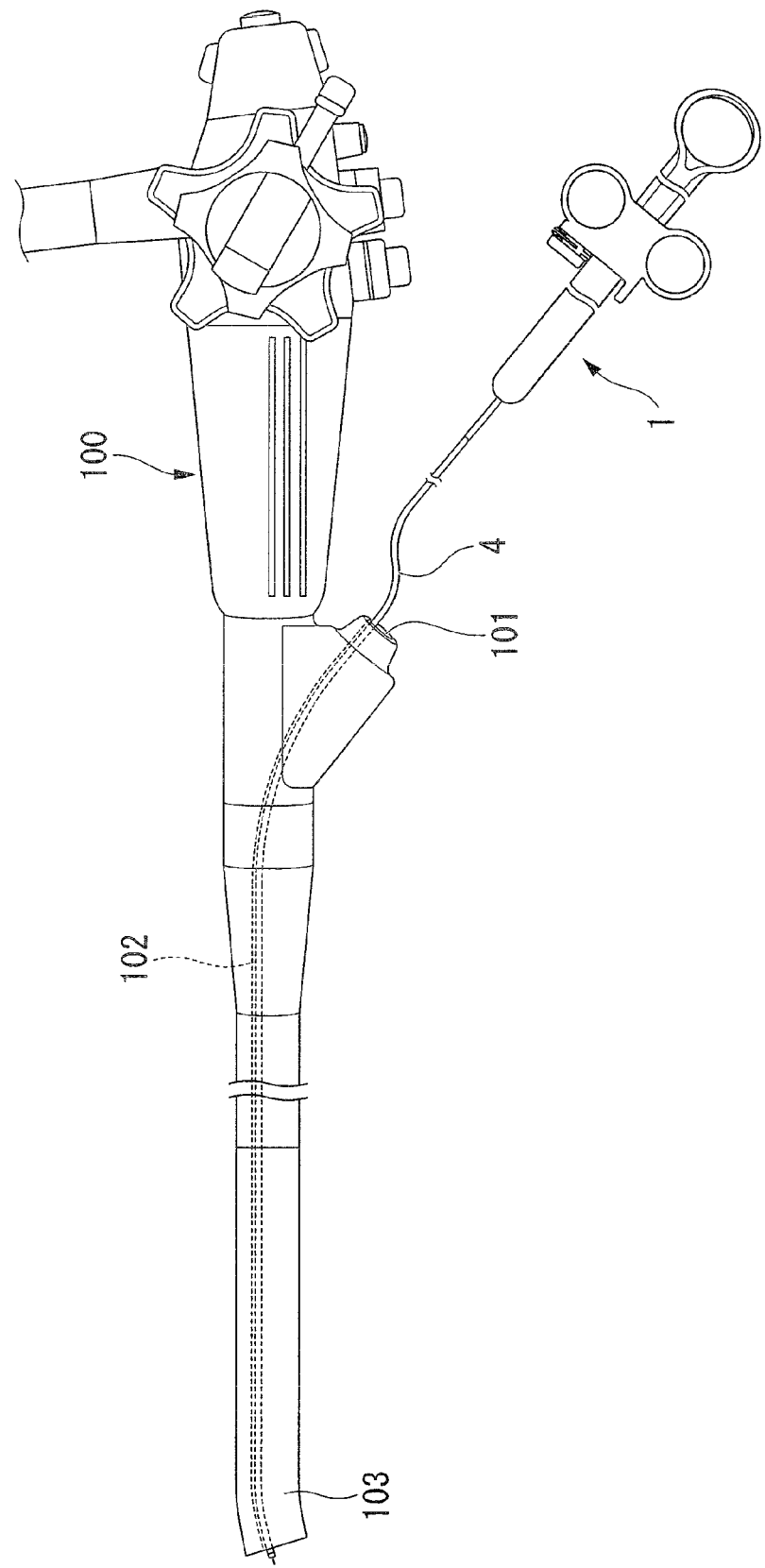
FIG. 5 is a view showing an arrangement in which the same treatment tool has been inserted into an endoscope.
Figure 6:
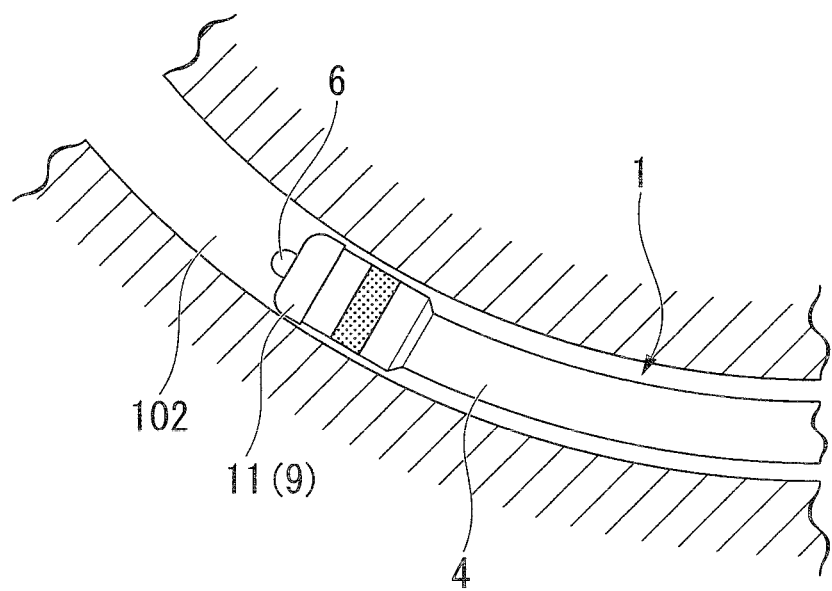
FIG. 6 is a view showing the distal end of the same treatment tool in the instrument channel of the endoscope.

The user retracts the slider 13 of the treatment tool 1 by pulling it fully toward the handheld side (ring 8B side), leaving only the large diameter part 6 of the knife 2 projecting out from the tip 11 of the distal member 9. The front end of the sheath 4 is then inserted into the instrument channel 102 via a forceps opening 101 which opens on the operator of the endoscope 100, as shown in FIG. 5.

Even if the inserted section 103 of the endoscope 100 twists, meanders or the like, inside the body cavity, the tip 11, which does not have angles or edges, comes into contact with the inner wall of the instrument channel 102 first, so that the inner wall of the body cavity is not damaged.

Further, it is preferable to design the outer diameter of the large diameter part 6 to be sufficiently small with respect to the outer diameter of the tip 11 so as not to come into contact with the inner wall of the instrument channel 102 even in the case of strong twisting, meanders or the like; for example, it is preferable to design the outer diameter of the large diameter part 6 to be one-half the size of the outer diameter of the tip 11. Note that even if the large diameter part 6 contacts the inner wall of the instrument channel 102, the large diameter part has a curved outer surface due to the semispherical part 6A and the circular cylinder part 6B, so that no injury is caused to the inner wall of the body cavity.

Further, the sheath 4 on the proximal end side is formed with a diameter which is smaller than the distal end part into which the distal member is inserted. Accordingly, it is possible to maintain a sufficient space interval between the sheath 4 and the instrument channel 102, and to effectively carry out suction or infusion of air, water, etc. using the instrument channel 102.

After the distal end of the treatment tool 1 is projected out from the endoscope 100, the user connects the plug 12 to a power cord, not shown in the figures. The power cord may also be connected in advance, prior to the insertion of the treatment tool 1 into the endoscope 100.

In the case where it is not possible to specify the tissue on which the procedure is to be performed due to difficulty in discriminating between the target tissue and the tissue surrounding it, the user may, as needed, facilitate visual confirmation of the boundary between the target and non-target tissue by applying a marking to the area around the target tissue. An example of the marking process will now be explained with reference to FIGS. 7(a) to 7(c). Note that in FIGS. 7(a) through 7(c), the outer edge of the target tissue T1 is clearly demarcated in order to facilitate the explanation.

Figure 7A:
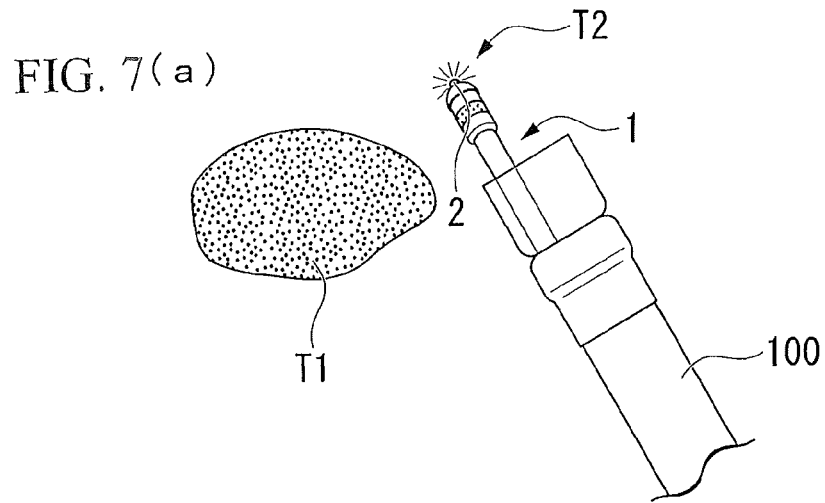
FIGS. 7 (a), (b), and (c) are all views showing the series of steps for marking using the same treatment tool.
Figure 7B:
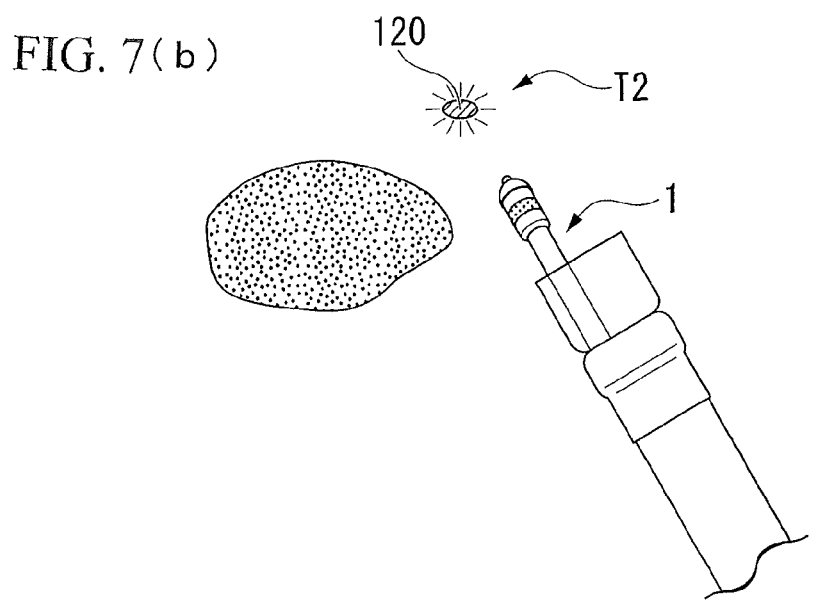

When performing the marking, the user maximally retracts the knife 2 and then transmits a high frequency current from the power source via the wire 3 to the knife 2, pressing the knife 2 into the non-target tissue T2 which is near the target tissue T1, as shown in FIG. 7(a). As a result, the large diameter part 6 is pressed into the non-target tissue T2, cauterizing the tissue that is in contact with the outer surface of the large diameter part 6. When the user moves the treatment tool 1 away from the non-target tissue T2, a marking scar 120 is formed as shown in FIG. 7(b).

Figure 7C:
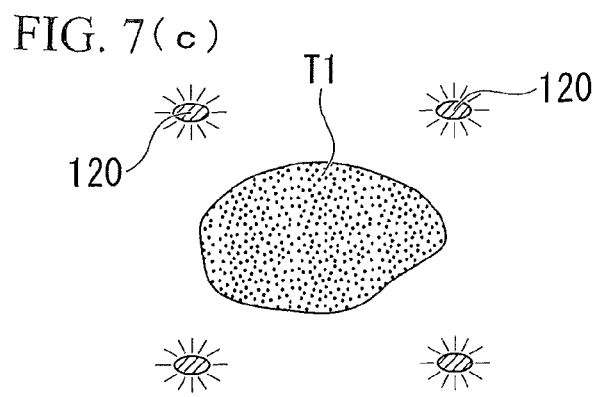

The user repeats the above operation multiple times to form a number of marking scars 120 sufficient to enable the user to recognize the outer edge of the target tissue T1, as shown in FIG. 7(c), after which the marking operation is concluded.

With the conventional treatment tool, it is not easy to press the knife into the non-target tissue while maintaining the knife in a state of projection at a length that is suitable for marking. As a result, marking is not a simple procedure. Further, the distal end surface of a substantially round rod-like knife is small, so that it was sometimes not possible to form the marking scar to be large enough to enable easy recognition.

In the treatment tool 1, a large diameter part 6 which cannot pass through the through hole 11A of the distal member 9 is provided to the distal end of the knife 2. Accordingly, it is possible to expose only the large diameter part 6 and easily create an optimal condition for marking by means of the user simply pulling the slider 13 to the maximum extent toward the hand-held side. Even if the knife presses against the tissue in this state, the cauterized area does not become deeper than necessary. Thus, marking can be carried out more safely.

The large diameter part 6 has a semispherical part 6A and a circular cylinder part 6B. Accordingly, when the large diameter part 6 is pressed into the tissue, a surface area larger than that of the knife 2 contacts the tissue and cauterizes it. As a result, the size of the marking scar 120 that is formed is suitably large, making it possible to carry out a marking which is easier to recognize visually.

Figure 8:
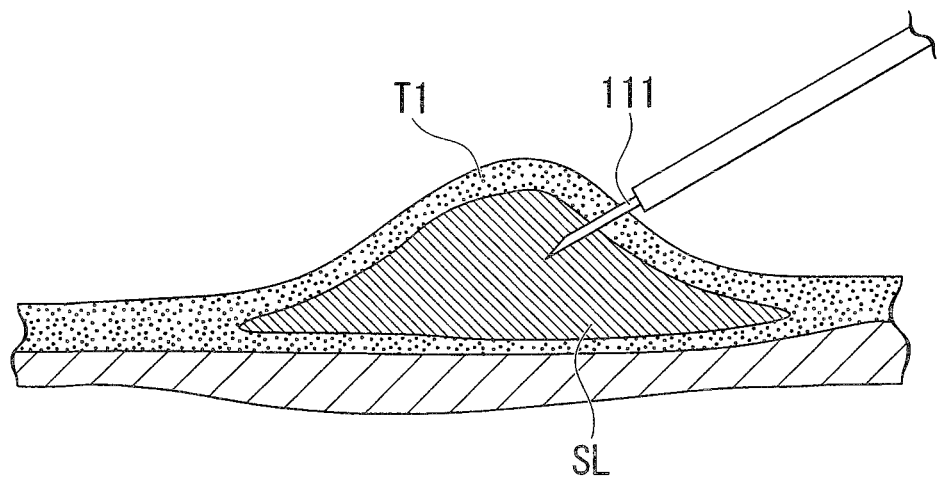
FIG. 8 is a view showing a manipulation in which the tissue is expanded in a technique using the same treatment tool.

Next, using a separate treatment tool having an injection needle 111, the user injects physiologic saline SL or the like under the target tissue T1 as shown in FIG. 8, causing the target tissue T1 to rise above the submucosa, etc.

Next, the user cuts around the entire circumference (referred to as "circumferential incision" hereinafter) of the target tissue T1 using the treatment tool 1.

By pushing in the slider 13 until the connecting member 7 comes into contact with the distal member 9, and advancing the wire 3, the user is able to project out the knife 2 from the front end of the sheath 4 to its maximum projecting length and hold the knife in this state.

Figure 9:
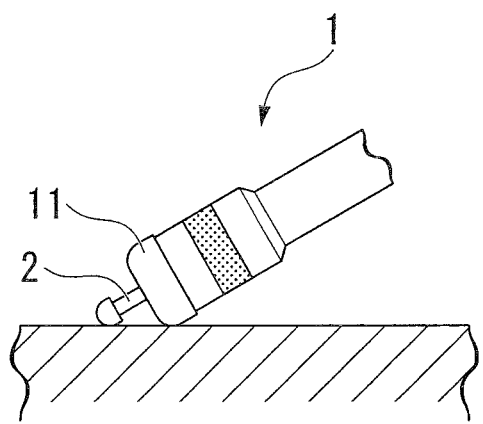
FIG. 9 is a view showing the action of the same treatment tool during use.

The distal end side of the tip 11 is formed to have a curved shape. As a result, as shown in FIG. 9, the distal end of the treatment tool 1 can more closely approach the tissue as compared to the case where the distal end side has a shape which has angles or edges. For this reason, even a knife 2 which projects out only a few millimeters can be easily brought into contact with the tissue. Further, the distal end side of the tip 11 is substantially in the shape of a circular arc. As a result, the knife 2 can be brought into contact with the tissue by approaching the tissue with the distal end of the treatment tool 1, regardless of the angle formed by the treatment tool 1 and the surface of the tissue.

Figure 10:
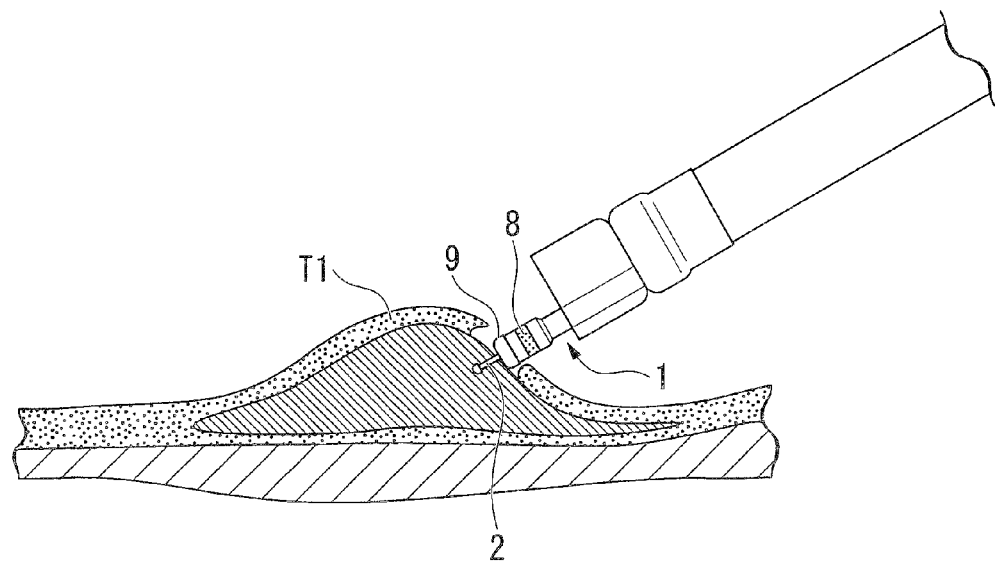
FIG. 10 is a view showing the action of the same treatment tool during use.

As shown in FIG. 10, with the knife 2 piercing the tissue, the distal end of the treatment tool 1 is moved along the periphery of the target tissue T1 to carryout the circumferential incision. The diameter of the proximal end side of the knife 2 is expanded by the distal member 9 which has a diameter that is larger than that of the knife 2, so that the knife 2 does not enter into the tissue more than is necessary.

In addition, the user confirms the position of the marker 8, and is thereby able to easily recognize how far into the tissue the distal end of the treatment tool 1 has advanced.

Figure 11:
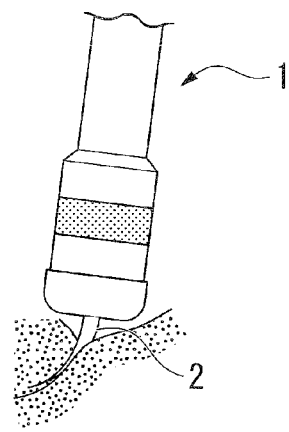
FIG. 11 is a view showing the action of the same treatment tool during use.
Figure 12:
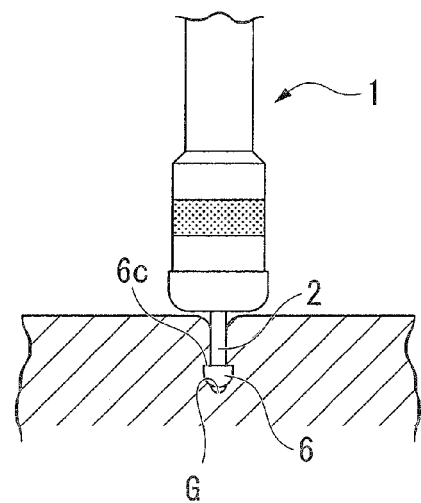
FIG. 12 is a view showing the action of the same treatment tool during use.

During the circumferential incision, the knife 2 is buried within the tissue as shown in FIG. 11. However, the large diameter part 6 is provided to the distal end of the knife 2, and projects outward so that the proximal end 6C of the circular cylinder part 6B has an edge. As a result, as shown in FIG. 12, the large diameter part 6 engages with the tissue and cannot be pulled out from the tissue unintentionally. In the conventional treatment tool, it is not easy to carry out circumferential incising of the target area while keeping the knife advanced at a specific length into the tissue. However, in the treatment tool 1 according to the present embodiment, if the circumferential incision of the target tissue is carried out by slightly retracting the knife 2 to form a space interval G between the target tissue and the knife 2, then the knife does not inadvertently pull out from the tissue, and the procedure can be carried out more easily and safely.

Figure 13:
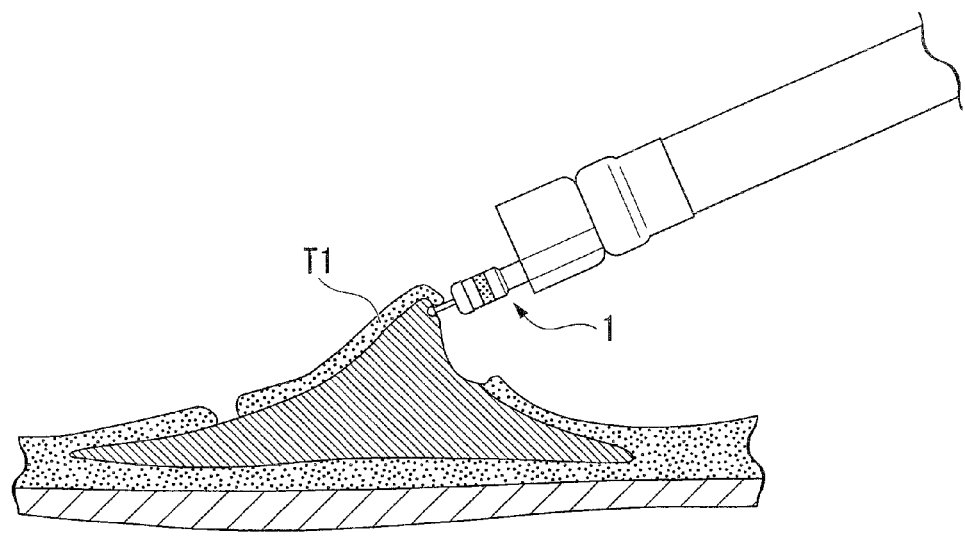
FIG. 13 is a view showing the action of the same treatment tool during use.

Once the circumferential incision is completed, the user applies upward traction on the target tissue T1 as shown in FIG. 13, and then removes the target tissue T1 by cauterizing from below.

Figure 14:
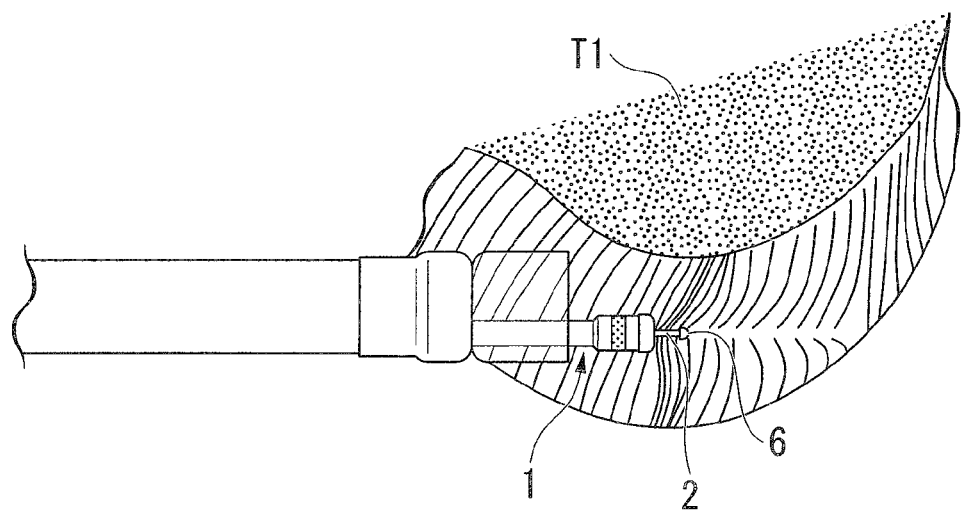
FIG. 14 is a view showing the action of the same treatment tool during use.

At this time, the user advances the incision by moving the treatment tool 1 recognize parallel to the surface of the stomach wall. However, as shown in FIG. 14, the large diameter part 6 of the distal end of the knife 2 is caught temporarily on the irregularities of the tissue, so that the knife 2 does not slip and separate from the tissue during the separating operation.

Figure 15:
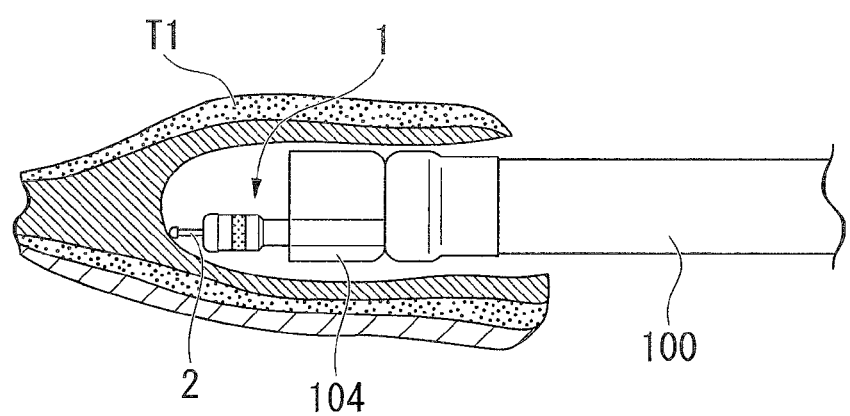
FIG. 15 is a view showing the action of the same treatment tool during use.

The user continues the above operation, separating the tissue as shown in FIG. 15, until the target tissue T1 is finally excised from the stomach wall. Next, using another treatment tool, etc., having a forceps, the excised tissue is recovered and the procedure is concluded.

Note that during the circumferential incision and separating techniques, a portion of the cauterized tissue may adhere to the knife 2, causing a decrease in the cauterizing efficiency. However, the through hole 11A of the distal member 9 has approximately the same outer diameter as the knife 2, so that the clearance (space interval G) is almost non-existent. Thus, by projecting and retracting the knife 2 several times by advancing and retracting the slider 13, it is possible to cause this cauterized debris to fall from the knife 2, and thus easily restore the cauterizing ability.

In various views including FIG. 15, a cap 104 is applied to the distal end of the endoscope 100 to maintain the endoscope's field of view and facilitate the technique. However, this cap 104 is not essential for the techniques described above and may be used only as needed.

In the treatment tool 1 according to the present embodiment, a large diameter part 6 is provided to the distal end of the knife 2. As a result, the movement of the knife 2 is stable due to the engagement of the large diameter part 6 in the tissue, even in the case where carrying out a separating operation on a target tissue such as mucosa. Accordingly, circumstances such as the knife slipping and inadvertently separating from the tissue do not readily occur, making it possible to more easily and with great certainty carry out various techniques, including separation of a target tissue such as mucosa or the like, that previously required a specific level of skill.

Further, as already described, due to the provision of the large diameter part 6, it is also possible to more easily and safely carry out such techniques as marking or circumferential incision.

One embodiment of the present invention was explained above. However, the present invention is not limited thereto. Rather, various modifications may be added provided that they do not depart from the spirit of the invention.

For example, the preceding embodiment explained an example in which a large diameter part was formed having a semispherical part on the distal end side and a circular cylinder part on the proximal end side. However, in place thereof, it is also acceptable to form the large diameter part using only the semispherical part 6A or the circular cylinder part 6B, as in the modification shown in FIGS. 16A and 16B. Further, in place of circular cylinder part 6B, the shape of the large diameter part may be an angular column, having a triangular or square shape when seen in a cross-section perpendicular to the axial direction. In this case, the diameter of the large diameter part changes depending on the cross section. However, provided that the diameter of at least one site is designed to be larger than the through hole 11A of the distal member 9, then the effects of the present invention can be obtained. In addition, the large diameter part may be formed to be in the shape of a sphere or circular cone, or to be in the shape of a triangular pole or a square pyramid or other such pyramidal form. Note that in the case where the large diameter part is in the form of a circular cone or pyramid, operations such as marking etc. can be more optimally carried out if the bottom surface is designated as the distal end side.

Figure 16A:
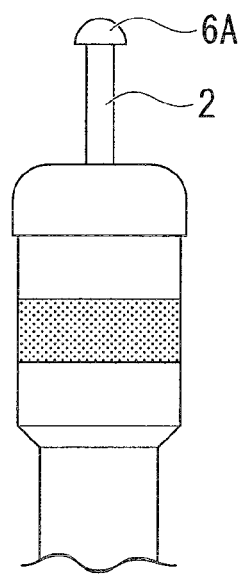
FIG. 16A is a view showing the distal end of the treatment tool according to a modification of the present invention.
Figure 16B:
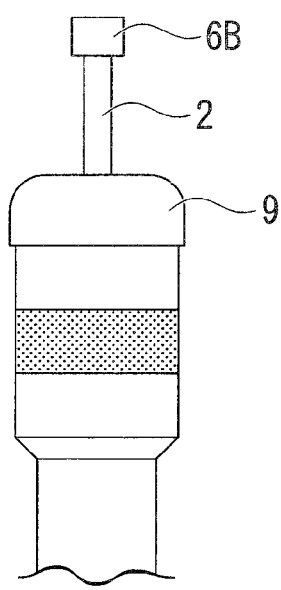
FIG. 16B is a view showing the distal end of the treatment tool according to a modification of the present invention.

Note that as shown in FIG. 16B, in the case where the large diameter part is formed so that the distal end side has an edge, the inner wall of the channel can be damaged when the large diameter part contacts the instrument channel of the endoscope. For this reason, it is preferable to design the various parameters of the large diameter part, including the diameter dimension, so that the large diameter part cannot easily contact the inner wall of the channel, such as by sufficiently decreasing the diameter of the large diameter part with respect to the outer diameter of the distal member 9, for example.

The preceding embodiment explained an example in which a technique was carried out using the treatment tool 1 at a site that is comparatively close to the distal end of the endoscope. However, provided that the sheath 4 has a specific rigidity, then a technique may be carried out on a tissue at a site distant from the endoscope 100, by projecting the sheath 4 out from the distal end of the endoscope 100 in a straight line. In this way, the treatment tool 1 is advanced and the technique may be carried out on a tissue located at a site where it is not easy to advance the endoscope.

The distal member is not essential in the treatment tool according to the present invention. Rather, it is acceptable to design the treatment tool so that the knife directly projects out from the distal end of the sheath. In this case, the thickness of the sheath and the diameter dimension of the large diameter part are suitably set, and the outer diameter of the large diameter part is made larger than the inner diameter of the sheath. As a result, the end surface of the distal end of the sheath and the proximal end of the large diameter part can come into contact. As a result, it is possible to easily maintain the arrangement in which only the large diameter part is exposed from the sheath, enabling the provision of a treatment tool with which marking and the like can be easily accomplished.

Note that in this case, it becomes easier for the large diameter part to come into contact the inner wall of the instrument channel as compared to the case where a distal member is present. For this reason, it is preferable to provide the large diameter part with a semispherical or spherical shape, etc., so that the large diameter shape does not damage the inner wall even if it comes into contact therewith.

Conventionally, when excising mucosa or the like using the endoscopic treatment tool disclosed in Japanese Unexamined Utility Model Application, First Publication No. S61-191012, the outer peripheral surface of the cutting section is brought into contact with the submucosal tissue and moved horizontally to advance cutting. However, when the cutting section is in the form of a rounded rod, the outer peripheral surface may readily slip, so that the cutting section may slide during the operation and separate away from the tissue. Accordingly, this is problematic as techniques such as excision, etc. using this endoscopic treatment tool are complicated and require skill.

However, when carrying out cutting or separating of tissue using the cutting section in the endoscopic treatment tool according to the present invention, the large diameter part engages in the tissue targeted for cutting and separating, or engages in periphery of the target tissue. As a result, slipping of the cutting section is prevented and movement of the treatment tool is stabilized.

Furthermore, since the large diameter part is provided with the semispherical part and the circular cylinder part, the outer surface of the large diameter part is formed by a curved surface only, so that injury is not easily caused to the tissue which is pressed into contact with the cutting section and the instrument channel of the endoscope into which the endoscopic treatment tool is inserted. As a result, the endoscopic treatment tool can be used more safely.

Furthermore, since the endoscopic treatment tool is provided with the tubular distal member, the distal end of the endoscopic treatment tool does not readily sink into the tissue, enabling more stable use and easier execution of various techniques by simply exposing only the large diameter part of the cutting section. Note that in this case, it is preferable to design the outer diameter of the distal member to be larger than the diameter of the sheath's inner cavity.

The endoscopic treatment tool according to the present invention prevents slipping of the knife during mucosal incision and separation particularly, and enables various techniques including removal of a target tissue such mucosa, which previously required a specific level of skill, to be carried out more easily and with greater certainty.

What is claimed:

1. A treatment tool comprising:
  a cutting section which is adapted to be endoscopically inserted into a body cavity and performs cutting procedures by transforming high frequency current, the entirety of the cutting section being conductive;
  a wire connected to the cutting section at a distal end of the wire;
  a sheath comprising an insulating material, the wire being inserted into the sheath;

a main body, a back end of the sheath being connected to the main body; and a slider to which a back end of the wire is fixed and which is disposed to the main body to enable sliding in an axial direction of the sheath, wherein the cutting section has a large diameter part at a distal end of the cutting section and a small diameter part proximal to the large diameter part, the large diameter part having an outer diameter such that the large diameter part is not capable of being accommodated in the sheath when the cutting section is maximally retracted along the axial direction toward the back end of the sheath, wherein the large diameter part includes at least a first portion and a second portion, the first portion at least partially including a circular cross-section formed in a direction orthogonal to a longitudinal axis of the cutting section at a distal end of the small diameter part and the second portion at least partially including a first rounded surface conductively connected to a circumference of the first portion, the second portion being disposed at a distal end of the first portion, wherein a tubular distal member having insulating properties is disposed on a distal end of the sheath, the tubular distal member including an insertion portion that is inserted into the sheath and a tip that is exposed outside the sheath, wherein the tip at least includes a second rounded surface, a radius of curvature of the second rounded surface being larger than that of the first rounded surface, and wherein when the cutting section is maximally retracted along the axial direction toward a proximal end of the sheath, a proximal surface of the second portion contacts with a distal end of the tip such that the large diameter is restricted to not to be accommodated in the sheath, the first rounded surface being more distal than the second rounded surface.

2. The treatment tool according to claim 1, wherein the first rounded surface of the second portion has a semispherical shape formed such that an apex of the semispherical shape is located on the longitudinal axis of the cutting section.

3. The treatment tool according to claim 2, wherein
the first portion is cylindrical and is provided to a proximal end side of the semispherical shape of the second portion so that an axis of the cylindrical first portion is parallel to an axis of the cutting section.

4. The treatment tool according to claim 1, further comprising:
the tubular distal member which has a through hole along the axis of the cutting section,
wherein a diameter of the through hole is smaller than the outer diameter of the large diameter part.

5. The treatment tool according to claim 4, wherein the outer diameter of the large diameter part is smaller than an outer diameter of the tip of the tubular distal member.

6. The treatment tool according to claim 5, wherein the outer diameter of the large diameter part is half the size of the outer diameter of the tip of the tubular distal member.

7. The treatment tool according to claim 4, wherein an outer diameter of the tubular distal member is larger than an outer diameter of the sheath.

8. The treatment tool according to claim 1, wherein the large diameter part has an outer diameter that is larger than an inner diameter of the sheath, the large diameter part projects out in the radially outward direction approximately 0.1-0.15 mm more than the outer peripheral surface of the small diameter part, and the small diameter part has a diameter of approximately 0.3-0.5 mm.

* * * * *